US00PP09416P

United States Patent [19]

Hesse

[11] Patent Number: Plant 9,416

[45] Date of Patent: Jan. 2, 1996

[54] CHRYSANTHEMUM PLANT NAMED 'ICEY ISLE'

[75] Inventor: Peter S. Hesse, Nipoma, Calif.

[73] Assignee: Clearwater Nursery, Inc., Nipomo, Calif.

[21] Appl. No.: 414,745

[22] Filed: Mar. 31, 1995

[51] Int. Cl.[6] ..... A01H 5/00

[52] U.S. Cl. ..... Plt./82.1

[58] Field of Search ..... Plt./82.1, 74.1

*Primary Examiner*—Howard J. Locker

*Attorney, Agent, or Firm*—Arnold, White & Durkee

[57] ABSTRACT

The present invention comprises a new and distinct cultivar of Chrysanthemum, botanically known as *Dendranthema grandiflora,* and referred to by the cultivar name Icey Isle.

1 Drawing Sheet

BACKGROUND OF THE NEW PLANT

Icey Isle originated from a cross made by Peter S. Hesse in a controlled breeding program at Clearwater Nursery, 887 Mesa Rd., Nipomo, Calif. 98444, USA.

The female parent of Icey Isle was the commercial variety Splendor (U.S. Plant Pat. No. 5,225) and the male parent was Hopscotch (U.S. Plant Pat. No. 5,816). Icey Isle was discovered and selected as one flowering plant within the progeny of the stated cross by Peter S. Hesse in Nov. 1989, in a controlled environment in Nipomo, Calif.

The first act of asexual reproduction of Icey Isle was accomplished in Jan. 1990, when vegetative cuttings were taken in a controlled environment at Clearwater Nursery, Nipomo, Calif., by Peter S. Hesse.

Horticultural examination of controlled flowerings of successive plantings has shown that the unique combination of characteristics as herein disclosed for Icey Isle are firmly fixed and are retained through successive generations of asexual reproduction.

Icey Isle has not been observed under all possible environmental conditions. The phenotype may vary significantly with variations in the environment such as temperature, light intensity and day lenth.

The following observations, measurements and comparisons describe plants grown in controlled environments at Clearwater Nursery, Nipomo, Calif. Unrooted cuttings were directly stuck into 6.5 inch pots and grown in a controlled environment under the natural temperature and day length prevailing in Jan. 1990 to March 1990.

The following traits have been repeatedly observed and are determined to be basic characteristics of Icey Isle which, in combination, distinguish this Chrysanthemum as a new and distinct cultivar.

1. Flat Capitulum Form.
2. Daisy Capitulum Type.
3. White fully expanded outer ray florets.
4. Yellow Daisy disc with green eye.
5. A diameter of 13.3 cm across the face of the capitulum.
6. Exceptional upright to spreading habit with an average of 3.0 breaks after a single pinch.
7. Flowering response is approximately 58 days from the start of short days.
8. Relatively easy to control plant height from bench such that the finished height will range from 40 to 45 centimeters depending on pot size and market requirements.

DESCRIPTION OF THE PHOTOGRAPH

The accompanying photograph shows typical inflorescence and leaf characteristics of Icey Isle with the colors being as nearly true as possible with illustrations of this type. The photograph shows Icey Isle grown as a pinched spray pot mum with five (5) cuttings in a 6.5 inch pot.

DESCRIPTION OF THE PLANT

Of the commercial cultivars known to the inventor, the most similar in comparison to Icey Isle are the cultivars Splendor and Hopscotch. Reference is made to Table I which compares certain characteristics of Icey Isle to the same characteristics of the above mentioned cultivars.

TABLE I

| CHARACTERISTIC | HOP-SCOTCH | ICEY ISLE | SPLENDOR |
|---|---|---|---|
| CAPITULUM FORMS | Flat | Flat | Flat |
| CAPITULUM TYPE | Daisy | Daisy | Daisy |
| DIAMETER ACROSS FACE | 7.5 cm | 13.3 cm | 12.2 cm |
| BRANCHING PATTERN | Upright Spreading | Upright Spreading | Upright Spreading |
| BREAKS/PINCH | 4.4 | 3.0 | 4.0 |
| HEIGHT IN 6.5" POT WITH 1–2 APPLICATIONS B-9 | 40–45 cm | 40–45 cm | 40–45 cm |
| RESPONSE: TREATMENT | 8.5 weeks medium vigorous grower | 8.5 weeks medium vigorous grower | 9.0 weeks medium vigorous grower |
| DISC FLORETS | | | |
| DISC FLORET COLOR | Yellow | Yellow | Yellow |
| NO. OF DISC FLORETS | 183.2 | 215.0 | 133.8 |
| LENGTH OF DISC FLORETS | 0.6 cm | 0.7 cm | 0.6 cm |
| RAY FLORETS | | | |
| COLOR | | | |
| FRONT: fully expanded | 9A Yellow | 155B White | 75A Purple |
| FRONT: unfolded ray florets | 9A Yellow | 155B White | 75A Purple |
| BACK: fully expanded outer ray floret | 6A Yellow | 155B White | 75D Purple |
| NUMBER | 32.6 | 46.0 | 52.3 |
| SHAPE | Elliptic | Elliptic | Elliptic |
| LENGTH | 3.85 cm | 5.9 cm | 5.2 cm |
| WIDTH | 1.43 cm | 1.7 cm | 1.5 cm |
| TOTAL NUMBER OF FLOWERS/ BREAK | 6.7 | 11.8 | 10.4 |

TABLE I-continued

| CHARACTERISTIC | HOP-SCOTCH | ICEY ISLE | SPLENDOR |
|---|---|---|---|
| LEAF | | | |
| COLOR: | Front: 147A Back: 147B | Front: 147A Back: 147B | Front: 139A Back: 138A |
| MATURE LEAF LENGTH: | Up to 10.2 cm | Up to 10.5 cm | Up to 8.4 cm |
| MATURE LEAF WIDTH: | 5.95 cm | 6.4 cm | 4.5 cm |

Similar traits of the three cultivars include: The large flat, daisy capitulum. The diameter of the capitulum of Icey Isle tends to be slightly larger than the capitulum of Splendor. Both Splendor and Icey Isle tend to have significantly larger diameter capitulums than Hopscotch. All three cultivars have similar upright, spreading branching patterns. Icey Isle tends to have fewer numbers of breaks per pinch per plant than both Hopscotch and Splendor. The finished plant height and the color of the disc florets is also similar for the three cultivars. Icey Isle tends to have more disc florets than either Hopscotch or Splendor. The length of the disc florets is also similar for the three cultivars. The front ray floret color of Icey Isle is white 155B, for Hopscotch is yellow 9A, and for Splendor is purple 75D. The back ray floret color of Icey Isle is white 155B, for Hopscotch yellow 6A, and for Splendor is purple 75D. Icey Isle has the largest number of ray florets followed by Splendor. Hopscotch has the fewer number of ray florets. The ray florets of all three cultivars are elliptic. Splendor and Icey Isle have similar length ray florets. Both cultivars have longer ray florets than Hopscotch. The width of the ray florets is similar for all three cultivars. The color of the leaves of Icey Isle are similar to Hopscotch. Icey Isle has the longest mature leaf length followed by Hopscotch, with Spendor having the shortest leaf. The three cultivars have similar leaf width. The response time from the start of short days is the same for Hopscotch and Icey Isle at 8.5 weeks. Response time is slightly higher for Splendor 9.0 weeks.

THE PLANT

Classification

*Botanical.*—*Dendranthema grandiflora.* Cultivar name: Icey Isle.

*Commercial.*—Flat daisy to be grown primarily as a Spray/CBR (center bud removed) or Disbud pot mum.

Inflorescence

*Capitulum.*—Form: Flat. Type: Daisy. Diameter across face: 13.3 cm.

*Ray florets.*—Color: White (general tonality within a distance of three (3) meters). Front: Fully expanded ray floret 155B. Front: Unfolded ray florets in center of flower. Back: Fully expanded outer ray floret 155B. Disc Floret Color: Edge begins with 14A to Center Green of 141C. Shape: Elliptic.

*Corolla of Disc Florets.*—Color: White.

Reproductive organs:

*Androecium.*—Present in disc floret; pollen: scant.

*Gynoecium.*—Present in both ray and disc floret.

General appearance:

*Height.*—When grown in a 6.5 inch pot with 1–4 applications of B-NINE™ at the rate of 2500 ppm, the total plant height from the bottom of the pot may be maintained at 40–45 cm.

Branching pattern: Upright and spreading with an average of 3.0 breaks when grown with one pinch.

*Foliage.*—Color: (upper surface) 147A. Color: (lower surface) 147B. Shape: (see photograph).

What is claimed is:

1. A new and distinct Chrysanthemum plant named Icey Isle substantially as herein described and shown, characterized by its white floret coloration and excellent upright spreading habit.

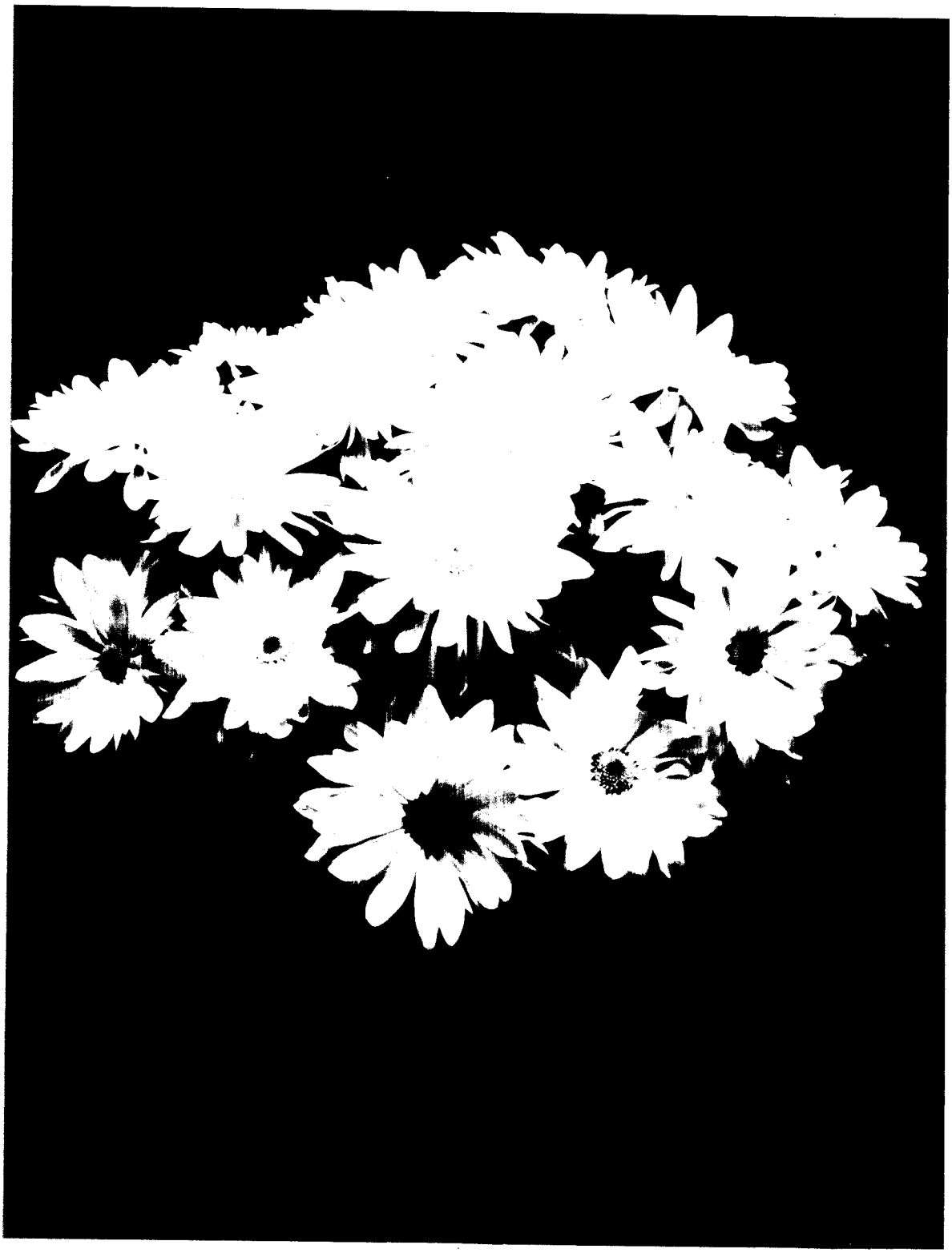

* * * * *